United States Patent
Meinel

[11] Patent Number: 6,051,797
[45] Date of Patent: Apr. 18, 2000

[54] FOOT PEDAL SWITCH ASSEMBLY FOR OPERATING A MEDICAL DIAGNOSTIC APPARATUS

[75] Inventor: Fred Meinel, Eckental, Germany

[73] Assignee: Siemens Aktiengesellschaft, Munich, Germany

[21] Appl. No.: 09/156,622

[22] Filed: Sep. 18, 1998

[30] Foreign Application Priority Data

Oct. 1, 1997 [DE] Germany .......................... 197 43 524

[51] Int. Cl.$^7$ ..................................................... H01H 3/14
[52] U.S. Cl. .......................................................... 200/86.5
[58] Field of Search .............................. 200/86.5, 61.89, 200/307; 74/512–514, 478, 478.5; 433/101, 113; 338/108, 153

[56] References Cited

U.S. PATENT DOCUMENTS

| | | | |
|---|---|---|---|
| 2,636,092 | 4/1953 | Schneider | 200/86.5 |
| 2,766,343 | 10/1956 | Heidman, Jr. | 200/61.29 |
| 2,872,542 | 2/1959 | Thompson | 200/86.5 |
| 3,663,772 | 5/1972 | Grabel et al. | 74/512 X |
| 3,742,167 | 6/1973 | Muther | 200/86.5 |
| 3,970,984 | 7/1976 | Grubenmann | 338/153 |
| 4,142,080 | 2/1979 | Takahashi | 200/307 X |
| 5,324,900 | 6/1994 | Gonser et al. | 200/86.5 |
| 5,422,521 | 6/1995 | Neer et al. | 200/86.5 X |

FOREIGN PATENT DOCUMENTS 25 30 108  10/1978  Germany .

*Primary Examiner*—J. R. Scott
*Attorney, Agent, or Firm*—Hill & Simpson

[57] ABSTRACT

A foot pedal switch for manually operating a medical diagnostic apparatus has a switch housing and a switching rocker with a neutral position that can be rotated around a rotational axle, with the rotational axle projecting from the housing such that it forms a bearing point of the foot pedal switch with its free end. The switching rocker is angled twice, and the axle has a semicircular outer region, so that, viewed laterally, a central rectangular surface of the switching rocker is secured on the straight surface of the rotational axle in a horizontally oriented fashion, while two lateral switching surfaces, which are rounded in front, project upwardly.

11 Claims, 3 Drawing Sheets

FOOT PEDAL SWITCH ASSEMBLY FOR OPERATING A MEDICAL DIAGNOSTIC APPARATUS

BACKGROUND OF THE INVENTION

1. Field of the Invention

The present invention relates to a foot pedal for a manually operating medical diagnostic device, of the type having a switch housing and with a switching rocker with a neutral position.

2. Description of the Prior Art

Foot pedals which are common in x-ray technology are composed of individual switch elements were assembled on a base plate corresponding to the required number of pieces. These switch elements are protected against unintentional actuation by a frame.

German OS 25 30 108 teaches a control apparatus for dental treatment devices with a foot pedal of this type, wherein the rotation axle for a rocker switch with a planar surface is installed in the foot pedal housing parallel to a base plate. The axle also performs a switching function in the direction of its longitudinal axis, so that a basic function—e.g. energizing the motor—is already triggered given application of the foot. After triggering, this basic function can be modified by lateral tilting of the sole of the foot.

SUMMARY OF THE INVENTION

An object of the present invention is to provide a foot pedal of the above general type particularly for radiology, wherein a number of switching functions can be detected or felt "blindly" and can be positively and reliably triggered, and wherein the primary switching surfaces lie at ground level in the non-actuated state.

The object is inventively achieved in a foot pedal wherein the rotational axle projects from the housing such that it forms a bearing or support point for the overall foot pedal assembly. The foot pedal thus lies with the back edge of the switch housing and the front part of the rotational axle on the ground, resulting in a stable 3-point bearing.

The main switching surfaces lie at ground level in the actuated as well as the non-actuated condition in an embodiment wherein the switching rocker is angled twice and the rotational axle has a semicircular outer region so that, viewed laterally, a central rectangular surface of the switching rocker is attached in a horizontally oriented fashion on the straight surface of the axle, while the two lateral switching surfaces, which can be rounded in front, project upwardly.

In a further embodiment the switch housing has an opening arranged above the axle with a switching tongue projecting therefrom.

Switching functions can be detected "blindly" and triggered positively and accurately by providing two switching surfaces separated by a ridge or projection arranged on the switch housing.

It has proven advantageous from an ergonomic perspective for the switch housing to be curved in a circular fashion such that the switching surfaces are adapted to lie in the region of a shoe rotating on its heel, worn by an operator.

The switch housing can have a bottom surface disposed in a beveled or slanted fashion relative to the other edges of the switch housing, which are perpendicular to one another, with the back part of the switch housing being higher than the front part, and the rotational axle of the switching rocker projecting from the front of the switch housing such that it its perpendicular thereto.

In an alternative embodiment the rotational axle of the switching rocker can be inclined forwardly such that its frontal region lies on the ground, so that the foot pedal is still supported on three points.

The switching functions can be increased in simple fashion in an embodiment wherein at least one switching module with a switch housing is attached laterally at the switch housing, with a rotational axle projecting from the side of the switch module housing oriented toward the switch housing of the foot pedal.

A rocker surface that has one can be angled attached at the rotational axle at the side thereof facing away from the switch housing.

An unintentional triggering of switching functions can be prevented by means of a limiting ridge attached to the switch housing terminating with the side facing the switch housing.

The versatility of the foot pedal can be increased further by combining an arbitrary number of switching modules with each other. Two switching modules with a dual rocker (two angled) surface, or even two switching modules with a rocker surface that has only one angle can be combined into one foot pedal combination.

DESCRIPTION OF THE PREFERRED EMBODIMENTS

Figure 1:
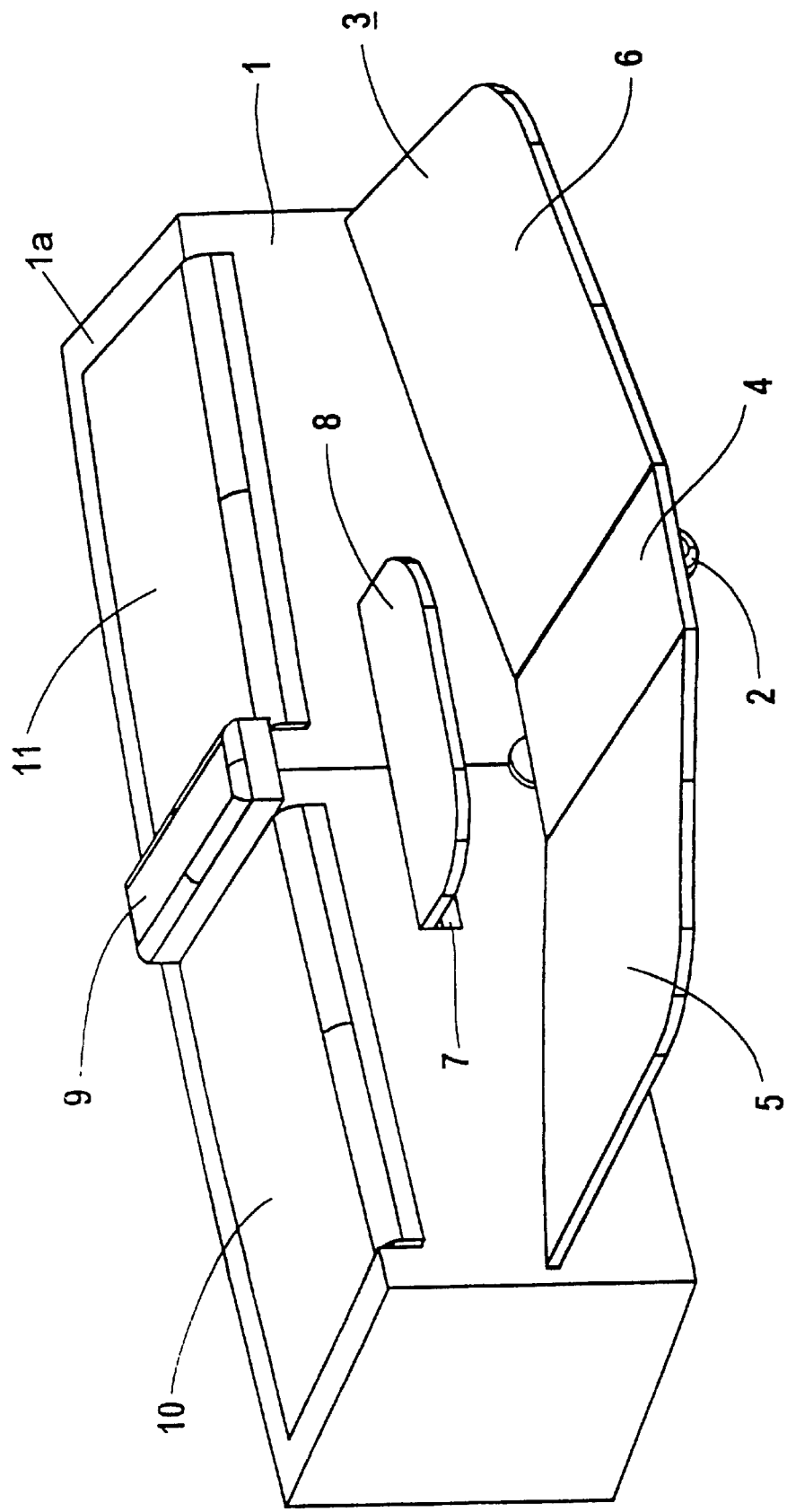
FIG. 1 is a perspective view of an inventive foot pedal.

FIG. 1 depicts a switch housing 1 of an inventive foot pedal, having a front which a rotational axle 2 projects. The axle 2 is semicircular in its outer region. A switching rocker 3 that is angled twice is attached at the surface of the axle 2, facing upwardly in a neutral position. The axle 2 is arranged such that, viewed laterally, the central rectangular surface 4 of the switching rocker 3 is oriented horizontally, while the two frontally rounded lateral switching surfaces 5 and 6 project upwardly. An opening 7 is provided above the exit of the axle 2 from the switch housing 1, a switching tongue 8 projecting therefrom. A projection 9 is attached to the switch housing 1 in the center, projecting from the top surface 1a of the switch housing 1. The switching surfaces of two foot buttons 10 and 11 are arranged laterally on opposite sides of the projection 9.

Figure 2:
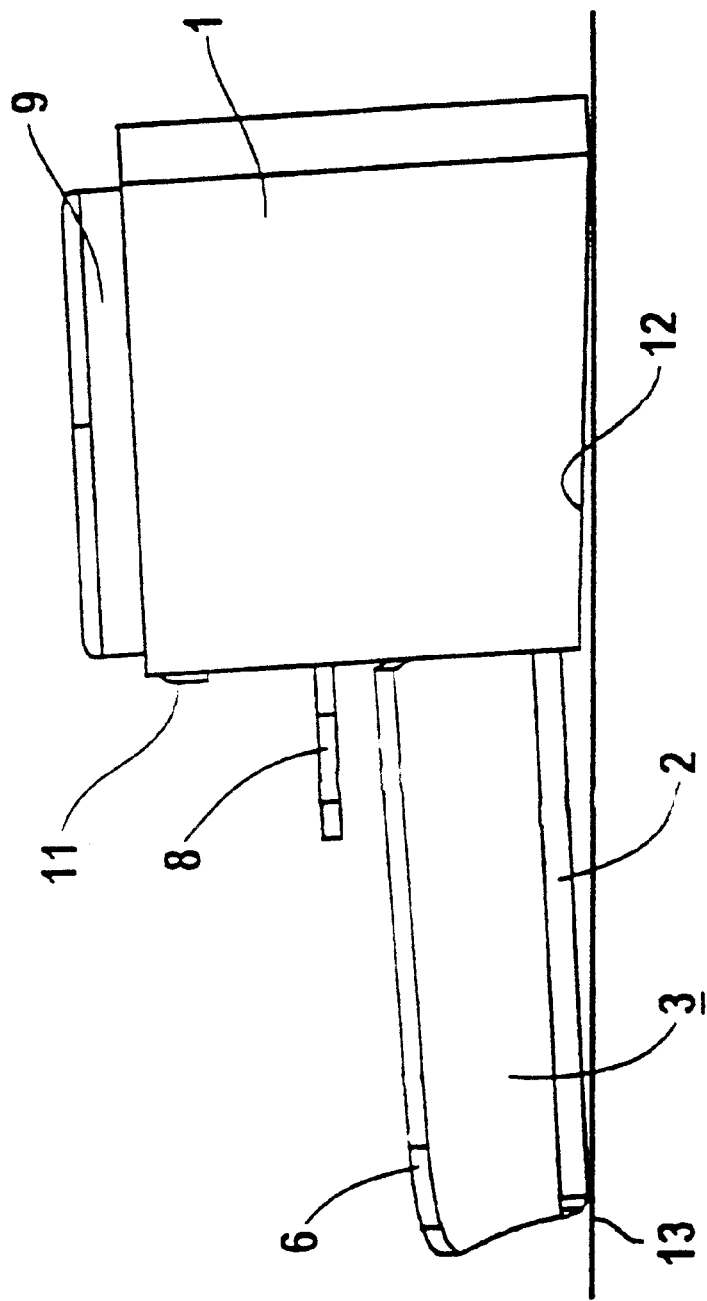
FIG. 2 is a side view of the foot pedal according to FIG. 1.

As is shown in FIG. 2, which depicts the inventive foot pedal in a side view, the switch housing 1 has a bottom surface 12 proceeding in beveled fashion relative to the other housing edges, which are perpendicular to one another, and the back part is higher than the front part. Since the axle 2 for the switching rocker 3 projects horizontally from the front, the foot pedal consequently lies with the back edge of the switch housing 1 and the front edge of the axle 2 on the ground 13, resulting in a stable 3-point bearing. If the back edge is constructed in arched fashion, or the bottom surface 12 is provided with bearing points (i.e., feet), a true 3-point bearing is obtained in all directions, so that if the ground 13 is uneven, placement and support of the foot pedal is not hindered.

Instead of the specific arrangement of the switch housing 1 shown in FIGS. 1 and 2, the rotational axle 2 can be inclined several degrees forwardly so that the foot pedal is still supported at three points.

Bearing structure for the axle 2 and a suitable mechanism for its neutral position are arranged in the switch housing 1. Switch elements that can be actuated by lever are arranged in the upper region of the switch housing 1. Electronics and sensors for a wireless signal transmission can be accommodated in the projection 9. Plug locations or a cable outlet for a hardwired electrical connection can be provided at the switch housing 1. By means of such an arrangement, a foot pedal for medical purposes is achieved which does still function even given a liquid level of 2.5 cm in the room.

Figure 3:
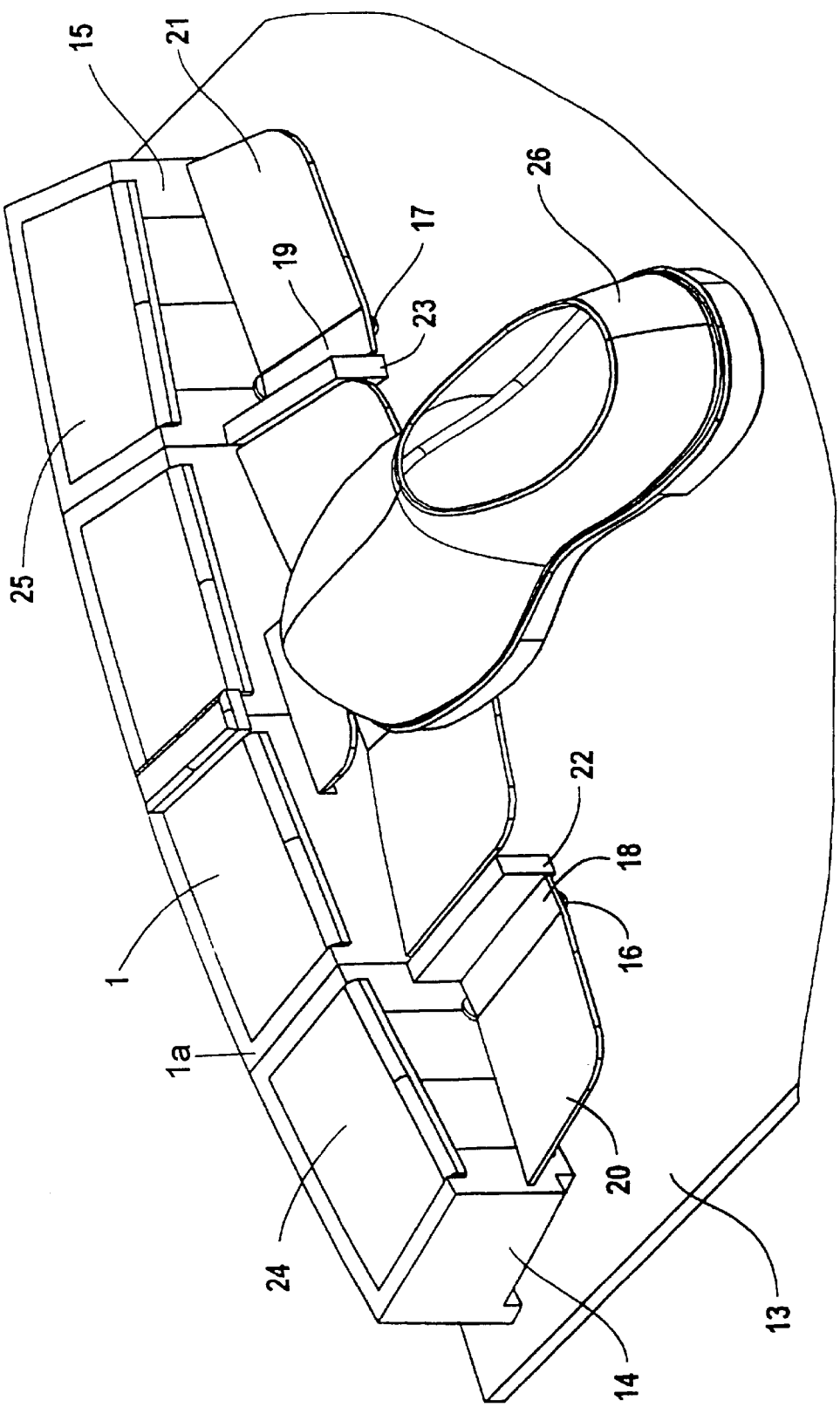
FIG. 3 shows an expanded embodiment of the inventive foot pedal.

FIG. 3 depicts another embodiment for neurological applications, for example, in which the foot pedal according to FIGS. 1 and 2 has been laterally expanded by switching modules. These switching modules have switch housings 14 and 15, respectively which are adapted to the switch housing 1 of the foot pedal, so that the general shape extends continuously. The rotational axles 16 and 17 projecting from the switch housings 14 and 15 are respectively arranged on the respective sides of the housings 14 and 15 facing toward the switch housing 1 of the initially-described foot pedal. The axles 16 and 17 respectively carry rectangular surfaces 18 and 19, at which only one angled rocker surface 20 and 21 is respectively arranged at the side facing away from the switch housing 1. Two limiting ridges 22 and 23 are attached at the side of the rectangular surfaces 18 and 19, these ridges terminating at the side of the housings 14 and 15 facing the switch housing 1. The switching surfaces of foot buttons 24 and 25 are provided on the switch housings 14 and 15 in the upper region. The surfaces of the switch housings 14 and 15 which are respectively oriented toward the switch housing 1 can likewise be provided with a ridge or projection.

To illustrate the operation of the inventive foot pedal, a shoe 26 is depicted which, in its resting position, lies on the rectangular surface 4 in front of the switching tongue 8 nearly at ground level on the ground 13 at a base plate. By turning the shoe 26 laterally at the ankle, the switching rocker can be correspondingly tilted, with the limiting ridges 22 and 23 preventing an accidental simultaneous actuation of the adjacently arranged rocker surfaces 20 and 21. By the simple raising of the tip of the shoe 26 and a forward displacement until the shoe 26 touches the ridge, the switching tongue 8 can be actuated, whereby the shoe 26 is located nearly on the level of the ground 13 again given stepping. By means of a blind detection of the projection 9 and corresponding lateral pivoting, one of the switching surfaces of the foot buttons 10 and 11 can be pushed.

If one of the laterally arranged switching modules is to be actuated, then the foot is pivoted in front of the switching rocker 3 so far to the side that the limiting ridges 22 and 23 are detected with the shoe 26. From there the rocker surfaces 20 and 21 can be actuated by means of further lateral pivoting of the shoe 26, or the foot buttons 24 and 25 can be actuated by means of corresponding raising of the shoe 26, whereby the ridges (not depicted) can form another orientation aid.

The shoe 26—(a European size 42 represented to scale relative to the foot pedal)—is positioned on the rocker pivot in the resting position. The total size of the foot pedal as well as the ergonomic, secure triggering of the switching rocker and of the switches lying thereabove thus can be recognized easily.

If such a foot pedal is employed in radiology it can execute the following switching functions, for example:

By means of ergonomic rotation at the ankle the function of transilluminating levels A or B is triggered, whereby the foot lies fully extended at ground level during the transillumination.

By actuating the switching tongue 8, two apparatuses can be simultaneously switched on. One apparatus can be operated in a high-contrast mode by means of the rocker surfaces 20 and 21. With the foot buttons 10 and 11 a recording can be performed and the brightness can be dimmed. The foot button 24 can effect a changeover of the individual modes of operation, and the foot button 25 can be provided for other auxiliary functions.

By means of the inventive development of the foot pedal a rocker circuit system is obtained with five switching functions, which can be increased to nine switching functions with two modules of the same constructional type. The specific shaping and the arrangement of projections 9 and ridges 22 and 23 enable a blind detection of the switching buttons without the danger of unintentional release of radiation. The detected rocker pivot or fulcrum can be stressed with the weight of the body without causing radiation to be emitted. The rocker surface is thus simultaneously an orientation aid and resting surface for the foot at "quasi ground level". The rocker surface does not constrain even the largest footwear, so that the switch length can be minimized to "two shoes long" without harming the security of the switch. A switch triggering for the transillumination of the levels A, B or A+B occurs ergonomically at "quasi ground level".

The foot pedal does not need a frame as is provided in known foot pedals in order to allow it to be shifted on the ground without an unintentional release of radiation. If the foot pedal falls or ends up on its back, the switching rocker 3 acts in a self-inhibiting manner so as to prevent an unintentional emission of radiation. Instances of unevenness of the ground are compensated by the 3-point bearing of rocker pivot/switch housing. The rocker surface that is tilted toward the operator improves the ergonomics and the design.

The disadvantages of existing foot pedals are avoided by means of the inventive device. A clear decrease in costs results due to the modular composition of the foot pedal. Switches can thus be prepared in simple fashion for a mono version, for a biplanar version, or even for an extended version for neurology.

It has proven to be ergonomically appropriate and practically sufficient to limit the number of modular units to four.

If two lateral switching modules of an extended version are combined, an arrangement with split rocker is obtained, which leads to another possibility for switching function.

Although modifications and changes may be suggested by those skilled in the art, it is the intention of the inventor to embody within the patent warranted hereon all changes and modifications as reasonably and properly come within the scope of his contribution to the art.

I claim as my invention:

1. A foot pedal for operating a medical diagnostic apparatus comprising:

a switch housing containing at least one switch;

a switching rocker disposed outside of said switch housing for manually actuating said switch, said switching rocker having a neutral position and being manually rotatable around an axis of rotation; and a rotational axle projecting from said switch housing and attached to said switching rocker at said axis of rotation, said switch housing and said rotational axle comprising an assembly, said switch housing having first and second support points for said assembly respectively on opposite sides of said rotational axle, and said rotational axle having a free end forming a third support point for said assembly co-planar with said first and second support points.

2. A foot pedal as claimed in claim 1 wherein said rotational axle is semicircular and has an upwardly facing flat surface, and wherein said switching rocker comprises a generally rectangular section attached to said flat surface of said rotational axle, and two lateral switching surfaces respectively disposed at opposite sides of said rectangular section and projecting upwardly at an angle relative to said rectangular section.

3. A foot pedal as claimed in claim 1 wherein said switch housing has an opening disposed above said rotational axle, and said foot pedal further comprising a switching tongue for actuating a switch inside said switch housing, said switching tongue projecting through said opening to the exterior of said housing.

4. A foot pedal as claimed in claim 1 further comprising a projection disposed at a top surface of said switch housing, and a first manually actuatable switching surface and a second manually actuatable switching surface disposed on said top surface of said switch housing at opposite sides of said projection.

5. A foot pedal as claimed in claim 1 wherein said switch housing comprises a curved front, facing said switching rocker, shaped to accommodate movement of a shoe rotating on a heel of the shoe disposed on said support surface.

6. A foot pedal as claimed in claim 1 wherein said switch housing comprises a front, a back, and opposite sides disposed perpendicularly relative to each other, and a bottom which is slanted between said back and said front with said back surface being adapted to rest on said support surface and said front being spaced from said support surface, and wherein said rotational axle projects perpendicularly from said switch housing.

7. A foot pedal as claimed in claim 1 wherein said rotational axle projects from said switch housing at an angle, so that said assembly is supported on three points, said three points including said support point formed by said free end of said rotational axle.

8. A foot pedal as claimed in claim 1 further comprising a switch module having a switch module housing disposed adjacent said switch housing at a side of said switch housing, said switch module housing having a switch module rotational axle projecting therefrom, disposed at a side of said switching rocker.

9. A foot pedal as claimed in claim 8 wherein said switch module rotational axle has a switch module rocker surface carried on said switch module rotational axle, said rocker surface being upwardly angled and extending away from said side of said switch housing at which said switch module housing is disposed.

10. A foot pedal as claimed in claim 9 further comprising a limiting ridge disposed on said rocker surface at a side thereof adjacent to said switch housing.

11. A foot pedal as claimed in claim 8 wherein said switch module is a first switching module, and said foot pedal further comprising a plurality of additional switch modules, each having a switch module housing, the respective switch module housings of said first switch module and said plurality of additional switch modules being disposed in succession at respective side of said switching rocker.

* * * * *